United States Patent [19]
Chin

[11] Patent Number: 5,096,554
[45] Date of Patent: Mar. 17, 1992

[54] NUCLEIC ACID FRACTIONATION BY COUNTER-MIGRATION CAPILLARY ELECTROPHORESIS

[75] Inventor: Allan M. Chin, Palo Alto, Calif.

[73] Assignee: Applied Biosystems, Inc., Foster City, Calif.

[21] Appl. No.: 390,631

[22] Filed: Aug. 7, 1989

[51] Int. Cl.$^5$ .................. G01N 27/26; B01D 57/02
[52] U.S. Cl. ........................ 204/180.1; 204/299 R
[58] Field of Search ............ 204/180.1, 183.3, 299 R

[56] References Cited
FOREIGN PATENT DOCUMENTS
60-259945 12/1985 Japan ............................ 204/180.1

Primary Examiner—John F. Niebling
Assistant Examiner—John S. Starsiak, Jr.
Attorney, Agent, or Firm—Peter J. Dehlinger; Joseph H. Smith

[57] ABSTRACT

A method of fractionating nucleic acid fragments is disclosed. The method is based on counter migration of the fragments in an upstream direction through a polymer solution which is moving by electroosmotic flow in a downstream direction. Fractionation of selected-size nucleic acid fragments can be enhanced by reducing the difference between the electroosmotic flow rate and the migration rates of the selected-size fragments.

19 Claims, 10 Drawing Sheets 1636 and bigger fragments
1018
506, 517, 396, 344, 298
220
201
154
134

ATAGCCGTATAAAGCCTA

NUCLEIC ACID FRACTIONATION BY COUNTER-MIGRATION CAPILLARY ELECTROPHORESIS

1. Field of the Invention

The present invention relates electrophoretic separation of nucleic acid fragments by capillary electrophoresis.

2. References

Cantor, C., et al., "Biophysical Chemistry Parts I, II and III", W.H. Freeman and Co., N.y. (1980)
Cohen, A.S., et al, Anal Chemistry, 59:1021 (1987).
Cohen, A.S., et al, J Chromatography, 458:323 (1988)
Compton, S.W., et al., BioTechniques, 6(5)432 (1988).
Kaspar, T.J., et al, J Chromatography, 458:303 (1988)
Lauer, H.H., et al., Anal Chem, 58(1):166 (1986).
Maniatis, , T., et. al., "Molecular Cloning: A Laboratory Manual", Cold Spring Harbor Labs (1982).
Maxam, A.M., et al., Meth Enzymol, 65:499 (1980)
Sanger, F., et al., Proc Nat Acad Sci, USA, 74:5363 (1977).
Smith, L.M., et al., Nature, 321:674 (1986).

3. Background of the Invention

Methods for size fractionating mixtures of single-strand or double-strand (duplex) nucleic acids are crucial to a variety of analytical and preparative techniques in biochemistry. One important example is restriction analysis, in which duplex DNA is digested with selected restriction enzyme(s), fractionated according to digest fragment size, then analyzed for fragment positions. This method is widely used in molecular cloning to determine the number and arrangement of restriction sites in a cloning vector, and to confirm insert location and/or orientation in the vector.

Restriction analysis is an important tool for genetic mapping as well, since it allows relatively long pieces of chromosomal DNA to be mapped, and ultimately sequenced, on the basis of restriction fragment sizes and overlap. In a related application, the discovery of linkages between a number of genetic diseases and restriction fragment length polymorphisms in humans has provided a tool for screening individuals for these genetic diseases.

Rapid DNA sequencing methods currently in use also rely on the ability to fractionate DNA fragments—typically single-strand fragments—on the basis of size. Both enzymatic sequencing techniques, in which random-termination fragments are generated enzymatically in the presence of dideoxynucleotides (Sanger), and chemical methods in which random-termination fragments are generated chemically (Maxam), rely on fractionation and discrimination of the fragments on the basis of fragment size. In particular, the fractionation method must be capable of distinguishing fragments which differ from each other by one nucleotide only.

In addition, size fractionation of nucleic acid fragments is valuable for isolating and purifying DNA or RNA fragments. In molecular cloning, it is common to fractionate restriction fragments to obtain selected fragments for vector construction. In oligonucleotide synthesis, it is generally desirable to purify fragments having the desired oligonucleotide sequence and subunit number.

Heretofore, standard methods available for size-fractionating nucleic acids fragments have used a solid or semi-solid gel matrix for electrophoretic fragment separation. In the case of larger molecular weight fragments, typically greater than about 1,000 bases, the preferred gel material is agarose, where the concentration of the agarose may vary from about 0.3%, for separating fragments in the 5-60 kilobase size range, up to about 2%, for separating fragments in the 100-3,000 basepair range (Maniatis). Smaller size fragments, typically less than about 1,000 basepairs, are usually separated in polyacrylamide gel. The concentration of acrylamide polymer can range from about 3.5%, for separating fragments in the 100-1,000 basepair range, up to about 20%, for achieving separation in the size range 10-100 basepairs.

More recently, DNA fragment separation by capillary electrophoresis (CE) has been proposed (Cohen, 1987, 1988, Compton, Kaspar). In one approach (Kaspar), fragments are separated in a gelled polyacrylamide medium within the tube. This approach shares many of the limitations of conventional acrylamide or agarose electrophoresis: the inconvenience of handling a polymerized gel, relatively long run times, and narrow size distribution of fragments which any given concentration of gel is capable of resolving.

Alternatively, it has been proposed to carry out fragment separation by CE in a buffer solution, without any separation medium (Cohen, 1987, 1988, and Compton). Generally, this approach has not produced consistent or easily interpretable results.

4. SUMMARY OF THE INVENTION

It is one general object of the present invention to, for size-fractionating nucleic acid fragments, a method which substantially overcomes or reduces the above-noted limitations associated with nucleic acid electrophoretic fractionation methods.

A more specific object of the invention is to provide such a method which gives high resolution, can be completed with short fractionation times, and requires only picogram amounts of fragment sample material.

Still another object of the invention is to provide such a method which can be carried out under a variety of variable electrophoresis conditions, some adjustable during an electrophoretic run, to optimize separation between or among selected size fragments.

It is yet another object of the invention to provide such a method in which the effective fractionation length of the electrophoretic pathway is substantially longer than the physical length of the capillary tube used for the fractionation, due to counter-migration of nucleic acid fragments in a polymer solution, in one direction, as the solution is drawn through a capillary tube by electroosmotic flow in the opposite direction.

In practicing the method, a liquid sample of nucleic acid fragments is loaded into one end of a capillary tube filled with a fluid electrolyte solution. The inner surface of the tube is negatively charged at the pH of the solution. One end of the tube is placed in fluid communication with a cathodic reservoir and the other end of the tube, in communication with an anodic reservoir containing a polymer solution of an uncharged or slightly charged polymer having a molecular weight of at least about 10,000 daltons, or alternatively, is characterized by a viscosity of at least about 15 centipoise in a 2% solution at room temperature. Preferred polymers have molecular weights of about 50-200 kilodaltons, and are characterized by a viscosity of about 1,000–5,000 centipoise in 2% solution at room temperature.

A voltage applied across the reservoirs is effective to draw the polymer solution into and through the tube by electroosmotic flow. The fluid flow rate in the tube is greater, in the direction of the cathodic reservoir, than the molecularweight dependent rates of migration of the nucleic acid fragments, in the direction of the anodic reservoir. As a result, the larger molecular weight nucleic acid fragments move more rapidly toward the cathodic reservoir than smaller fragments, and the total migration distance of all of the fragments relative to the separation medium (the polymer fluid) is substantially greater than the total length of the capillary tube.

The degree of fractionation of the nucleic acid fragments can be enhanced, according to one aspect of the invention, by selectively adjusting the rate of electroosmotic flow of polymer solution through the tube, to reduce the difference between the flow rate and the migration rate of the selected molecular weight fragments, subject to the constraint that the rate of electroosmotic flow is greater than the upstream migration rate of the slowest fragment to be fractionated. The effect of differentially decreasing electroosmotic flow rate or increasing fragment migration in the opposite direction is to increase the effective length over which electrophoretic migration of the fragments can occur.

The rate of electroosmotic flow of polymer solution through the tube can be adjusted, in one embodiment, by changing the pH of the electrolyte and polymer solutions to control the density of negatively charged groups on the inner wall of the tube. Increasing or decreasing the negative charge density on the tube wall increase or decrease, respectively, the rate of electroosmotic flow. Alternatively, the rate of migration of larger molecular weight species can be increased by reducing the concentration of polymer in the solution. The neutral polymer used in the method is preferably a polysaccharide, such as a modified cellulose, whose molecular weight is at least about 100,000 daltons, or, alternatively, which is characterized by a viscosity, in a 2% polymer solution at room temperature, of at least about 3,000 centipoise.

The applied voltage may be pulsed at one or more selected frequencies. According to one aspect of the invention, it has been discovered that applying a pulsed voltage of a given frequency produces two divergent types of migration rate changes with respect to migration rate s in a constant-voltage field For fragments having relatively large sizes, the rate of migration is progressively decreased, with respect to the migration time in a constant-voltage field, with increasing fragment size. This behavior is consistent with a model based on inertial effects in which larger fragments are, on average, slower to recover thir constant-field velocities.

For fragments having relatively small sizes, on the other hand, the rate of migration is actually increased with respect to the migration time in a constant-voltage field, with decreasing fragment size. This behavior cannot be explained by inertial effects alone. This phenomenon can be exploited in a variety of ways to enhance separation of selected-size nucleic acid fragments. For example, to isolate fragments in a selected size range, the pulse voltage frequency can be set initially to preferentially separate the desired fragments from larger molecular weight species. The frequency is then adjusted to separate the desired fragments from smaller molecular weight species.

In another aspect of the invention, the resolution of fragments in the counter-migration system, and particularly small duplex fragment, can be enhanced by binding the fragments to be separated with an intercalating agent, such as ethidium bromide or acridine orange.

These and other objects and features of the invention will become more fully apparent when the following detailed description of the invention is read in conjunction with the accompanying drawings.

DETAILED DESCRIPTION OF THE INVENTION

A. Capillary Electrophoresis System

Figure 1:
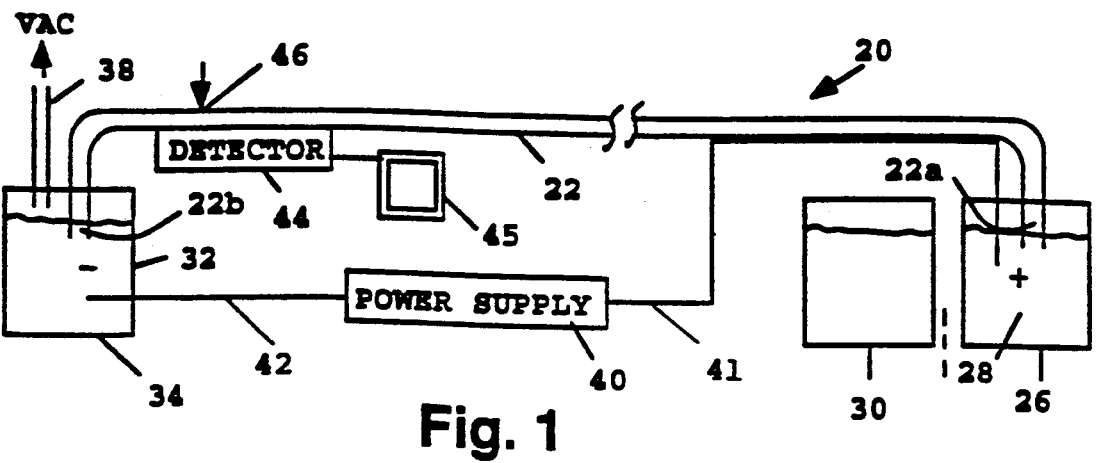
FIG. 1 is a schematic diagram of a counter-migration capillary electrophoresis system used in practicing the method of the invention.

FIG. 1 is a simplified schematic view of a capillary electrophoresis system 20 suitable for practicing the method of the invention. The system includes a capillary tube 22 having a length preferably between about 10-200 cm, typically less than about 100 cm, and an inner diameter of preferably between about 25-200 $\mu m$ (microns), typically about 50 $\mu m$. In the embodiment shown, the tube is supported in a horizontal position and has downwardly bent end regions.

The inner surface of the tube has chemical groups which are negatively charged at the a pH preferably between about 4-9. The surface chemical groups may be an inherent property of the capillary material, such as is the case for a fused silica tube which has surface silane groups. Alternatively, or an addition, the capillary walls may be treated with known derivatization reagents for covalent attachment of negative chemical groups, such as acid groups, to the inner capillary walls, or with known negatively charged surface-coating agents. Methods for derivatizing or coating glass or the like are well known. One preferred capillary tube is a fused silica tube having an inner diameter of 50 $\mu m$ and available from Polymicro Technologies (Phoenix, AZ).

More generally, the capillary tube may be any tube or channel capable of supporting a column of polymer solution, preferably at a column thickness of 200 $\mu m$ or less. For example, the tube may take the form of a channel formed in a glass slide or the like, and having negatively charged surface groups A anodic reservoir 26 in the system contains an electrolytic polymer solution 28 (Section II) which is drawn through the tube by electroosmotic flow during electrophoresis, as will be described in Section III. The anodic end of the tube, indicated at 22a, is immersed in the polymer solution, as shown, during electrophoresis.

A sample reservoir 30 in the system contains the nucleic acid fragment mixture which is to be loaded into the cathodic end of the tube. Preferably the sample material is dissolved in the electrolytic solution or in water. The sample and cathodic reservoirs may be carried on a carousel or the like, for placement at a position in which the lower cathodic end of the tube can be immersed in the reservoir fluid. Although not shown here, the carousel may carry additional reservoirs containing solutions for cleaning and flushing the tube between electrophoretic runs or different polymer solutions, where two or more polymer solutions are employed in a single electrophoretic fractionation method.

The opposite, anodic end of the tube, indicated at 22b, is sealed within an anodic reservoir 32 and is immersed in an anodic electrolyte solution 34 contained in the reservoir, as shown. The a second tube 38 in the reservoir is connected to a finely-controlled vacuum system (not shown) for drawing fluid, e.g., washing and cleaning solutions, electrophoresis polymer solution, through the tube and for loading the nucleic acid sample material in reservoir 30 into the tube.

A high voltage supply 40 in the system is connected to the cathodic and anodic reservoirs as shown, for applying a selected electric potential between the two reservoirs. The power supply leads are connected to platinum electrodes 41, 42 in the cathodic and anodic reservoirs, respectively. The power supply may be designed for applying a constant voltage (DC) across the electrodes, preferably at a voltage setting of between 5-50 KV. Alternatively, or in addition, the power supply may be designed to apply a selected-frequency, pulsed voltage between the reservoirs. In general, the shorter the capillary tube, the higher the electric field strength that can be applied, and the more rapid the electrophoretic separation. When operated in a pulsed voltage mode, the power supply preferably outputs a square wave pulse at an adjustable frequency of about 50 Hz up to a KHz range, and an rms voltage output of about 10-30 KV. Higher pulse frequencies, even into the MHz range may be suitable for some applications. Exemplary DC and pulse-voltage power supplies are described in Examples 1 and 8, respectively.

Completing the description of the system shown in FIG. 1, a detector 44 in the system is positioned adjacent the anodic end of the tube, for optically monitoring nucleic acid fragments migrating through an optical detection zone 46 in the tube. The detector may be designed either for UV absorption detection and/or for fluorescence emission detection. UV absorbance is typically carried out at 240-280 nm, using, for example, a Kratos 783 UV absorbance detector which has been modified by Applied Biosystems (Foster City, CA.), by replacing the flow cell with a capillary holder. Fluorescence emission detection is preferably carried out at a selected excitation wavelength which is adjustable between about 240-500 nm, depending on the fluorescent species associated with the nucleic acid fragments, as discussed below. One exemplary fluorescence detector is an HP1046A detector available from Hewlett-Packard (Palo Alto, CA), and modified as above for capillary tube detection. The detector is connected to an integrator/plotter 45 for recording electrophoretic peaks.

In operation, the capillary tube is thoroughly washed by drawing suitable cleaning and rinsing solutions through the tube by applying a vacuum to reservoir 32, such as detailed in Example 1. The tube is then flushed with several volumes of the electrolytic polymer solution and a small volume, typically 1-10 nanoliters of sample material is loaded into the cathodic tube end. A voltage is applied between the cathodic and anodic reservoirs until all of the fragment peaks have passed through the detection zone.

In one embodiment of the method, described in Section C below, enhanced electrophoretic separation of the nucleic acid fragments is achieved by driving the electrophoretic process with a pulsed voltage at a selected frequency, e.g., 300-1,000 Hz. In one preferred method, a pulsed voltage is applied until the leading (most downstream) band is just upstream of the detection zone, and then the system is switched to a DC mode, to reduce noise at the detector, until all of the bands have been recorded.

Figure 2:
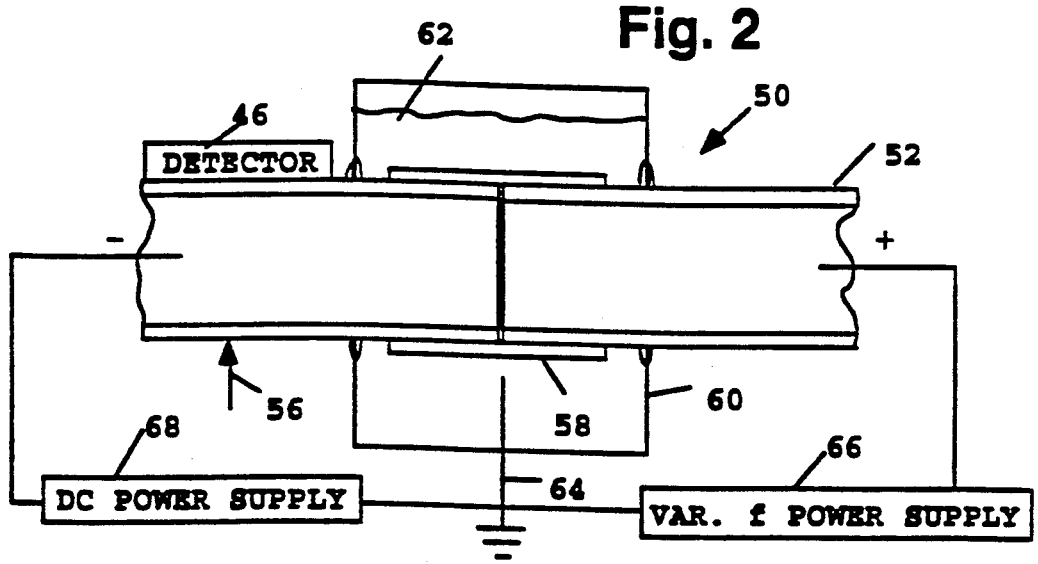
FIG. 2 is a schematic view of a capillary electrophoresis system designed for operation simultaneously in both a pulsed and constant-voltage mode.

FIG. 2 shows a fragmentary view of an electrophoretic system 50 which can be operated to the end of the electrophoretic run under a pulsed field. The capillary tube 52 in the system has a small-clearance break 54 adjacent and upstream of the detection zone, indicated at 56. The tube sections on either side of the break are coupled by porous glass sleeve 58 which allows electrolyte migration into and out of the tube. The coupled portion of the tube is sealed within a reservoir 60 filled with a suitable electrolyte solution 62. A grounded electrode 64 in the reservoir is connected to the high-voltage side of a pulsed-voltage power supply 66 whose negative side is in communication with a suitable cathodic reservoir. The grounded electrode is 64 is connected to the high-voltage side of a DC power supply 68 whose negative side is in communication with a suitable anodic reservoir.

In operation, after sample material is loaded into the cathodic end of the tube, the pulsed-voltage power supply is adjusted to a desired voltage and frequency level, and the DC power supply to a desired voltage level. Nucleic fragments in the sample are fractionated under the pulsed field within the portion upstream of break 54. Thereafter, the fragments are carried in a constant-voltage field through the detection zone, where the fragments can be optically detected without pulse-frequency noise effects.

Although not shown here, it will also be appreciated that the electrophoresis system can be readily adapted for collecting nucleic acid fragments for preparative electrophoresis applications. Sample collection may be accomplished, for example, by providing a series of cathodic reservoirs into which the fragments can be eluted.

B. Polymer Solution

The electrolytic polymer solution used in the method is composed of electrolytes and a polymer which is effective to form a fluid fractionation matrix in the tube. In addition, the solution has a pH at which the charged surface groups on the inner wall of the tube are at least partially ionized in their deprotonated state. The pH of the solution is preferably between 4-9. The pH may be adjusted to achieve a desired degree of tube wall charge density as discussed in Section C below.

The electrolytes in the solution may include buffer components, typically at a 10 mM buffer concentration, salts, typically at a 5-10 mM concentration, and preferably a heavy metal chelator, such as EDTA. In addition, the solution may contain a denaturant, such as urea, which functions to minimize interactions among fragments and between fragments and the tube walls. One preferred polymer solution, described in Examples 1-8, includes as its buffer components 10 mM Tris-borate buffer, pH 8.3, 5 mM NaCl, 0.1 mM EDTA, and 7M urea. The solution may also include an intercalating agent, such as ethidium bromide, for a purpose to be described in Section C below.

The polymer in the solution is one which is effective, in a fluid, non-gelled state, of differentially retarding nucleic acid fragments on the basis of size, when the fragments are migrating through the matrix under the influence of an electric field. The polymers are uncharged, and have molecular weights of at least about 10 kilodaltons, and are characterized by a viscosity of at least about 15 centipoise in a 2% (weight percent) solution at room temperature. By uncharged polymer is meant a polymer which does not contain net positive or negative charges at the pH of the polymer solution, or which contains substantially fewer net negative or positive charges than one per polymer subunit.

One preferred class of polymers is polysaccharides, such as dextran and, in particular, water-soluble cellulose derivatives, such as hydroxypropylmethylcellulose (HPMC), hydroxyethylcellulose (HEC), and methylcellulose (MC). Preferred polymers have molecular weights of about 50-200 kilodaltons, and are characterized by a viscosity of about 1,000-5,000 centipoise in 2% solution at room temperature.

The weight percentage of polymer in the solution may vary from about 0.1 to up to 1% or greater, depending on the sizes of fragments to be fractionated and, where a pulsed field is used, the frequency of the applied field, as will be seen in Section D below.

C. Electroosmotic Flow

Figure 3:
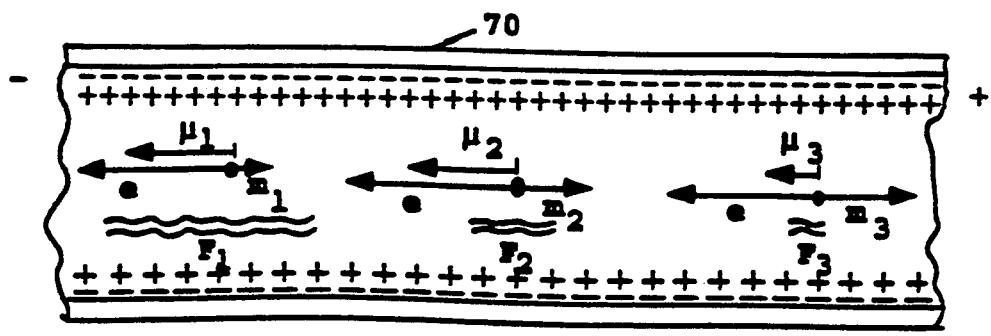
FIG. 3 is an enlarged, fragmentary portion of a capillary electrophoresis tube, illustrating electroosmotic flow (e) in a right-to-left direction, and fragment migration ($m_1$, $m_2$, $m_3$) in a left-to-right direction.

According to an important aspect of the invention, the fractionation of nucleic acid fragments in the capillary tube occurs by size-dependent migration of the fragments against the bulk electroosmotic flow of polymer solution in the tube. This phenomenon, which is referred to herein as counter-migration capillary electrophoresis (CMCE) in a polymer solution matrix, is illustrated in FIG. 3, which shows an enlarged, fragmentary portion of a capillary electrophoresis tube 70.

As seen in the figure, the negatively charged groups on the inner tube wall, indicated by "−" symbols, are shielded by positively charged ions in the polymer solution, essentially forming a positively charged shell about the column of fluid in the tube. The thickness of the shell of relatively immobilized positive ions at the wall surface is known as the shear distance This outer shell of positive charge and inner bulk phase charge distribution is called an electric double layer, and is characterized by a zeta potential, which is a measure of the potential between the outer shell of positive charges and the bulk medium.

Under the influence of an electric field, this column of polymer solution in the medium (which is surrounded by a shell of positive charges) is drawn electroosmotically in the direction of negative or low potential. The rate of electroosmotic flow in the tube is indicated by the arrow e in the figure (arrow e may be thought... of as a vector with a magnitude e and a direction along the axis of the tube). The electroosmotic flow rate e in a capillary tube can be described by the equation:

$$e = \frac{\epsilon \xi E}{\eta}$$

where $\epsilon$, $\eta$, $\xi$, and $E$ are the permittivity of the fluid, its viscosity, the zeta potential, and the electrical field strength, respectively. Under typical electrophoresis conditions, such as described in Example 1, the rate of electroosmotic flow in the tube is between about 0.0.1 and 0.5 cm/sec.

At the same time the polymer solution in the tube is moving downstream (toward the cathodic reservoir) by electroosmotic flow, the negatively charged nucleic acid fragments are migrating relative to the solution in the opposite direction toward the anodic reservoir. FIG. 3 shows the rates of migration of three different size duplex nucleic acid fragments $F_1$, $F_2$, and $F_3$ having decreasing sizes, e.g., 1,000, 300, and 50 basepairs, respectively. Because of molecular interactions of the fragments with the polymer molecules, the rates of fragment migration toward the anodic reservoir, indicated at $m_1$, $m_2$, and $m_3$ in the figure, are size dependent, with smaller fragments migrating faster in the anodic direction.

The net migration rate of the three fragments through the tube in the direction of the cathode is then the vector sum of the electroosmotic flow e and the size dependent migration m, indicated as $u_1$, $u_2$, and $u_3$ in FIG. 3. As seen, these net migration rates $u_i$ of the particles are size dependent, with the larger fragments migrating more rapidly toward the cathode than smaller fragments.

Figure 4:
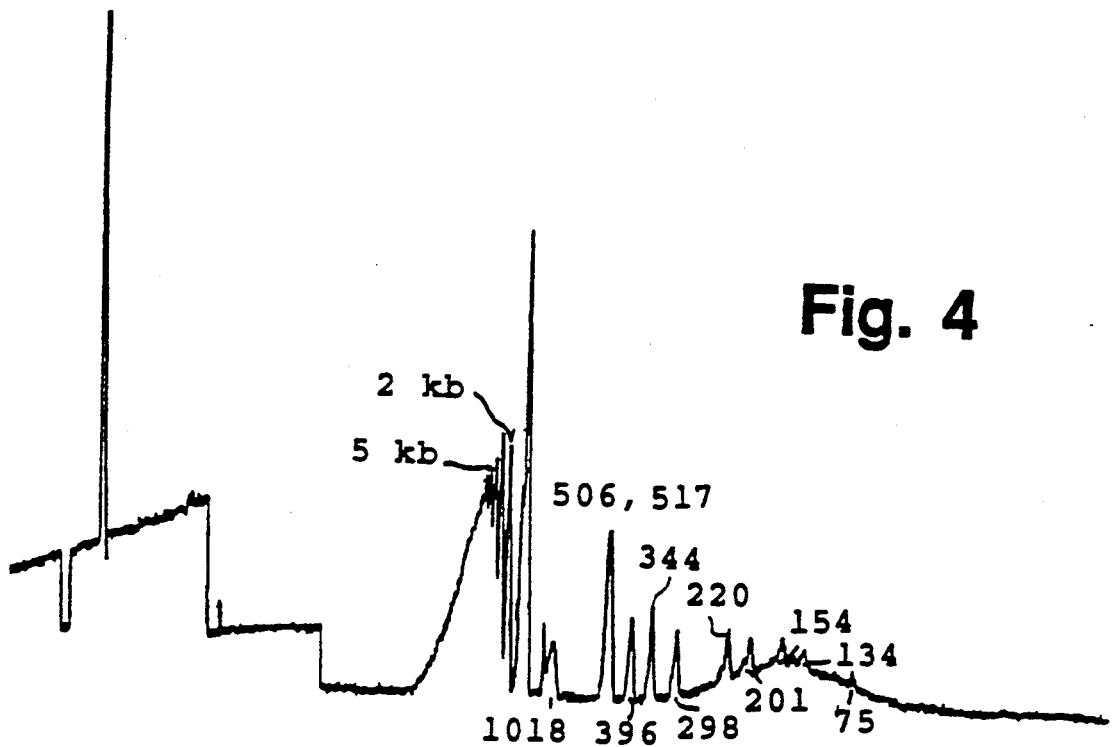
FIG. 4 is an electropherogram of duplex DNA fragments fractionated in accordance with the present invention, in 0.25 weight percent hydropropylmethylcellulose (HPMC) solution.

FIG. 4 shows an electropherogram of DNA restriction fragments containing 1 kb DNA ladder fragments (multiples of 1 kb fragments) and smaller HinfI fragments. The large spike at the left of the electropherogram is the leading edge of the water from the sample loaded into the tube initially. The migration times (time between start of electrophoresis and detection at the detection zone) is indicated above each peak. The fragment sizes (number of bases) are the bold numbers in the figure. As seen, larger fragments have shorter migration times. It is also noted that under the polymer and electric field conditions employed, the system was able to resolve fragments up to about 3 kbases, and to distinguish, but not baseline resolve larger fragments. It will be appreciated from FIG. 3 that the effective fractionation distance—that distance which a fragment travels through the polymer matrix—can be selectively increased, to enhance the fractionation of that fragment, by varying the relative rates of electroosmotic flow and upstream fragment migration during electrophoresis. In particular, as the rate of electroosmotic flow e and the rate of upstream migration $m_i$ of a fragment $F_i$ approach a common value, the actual fragment migration rate $u_i$ becomes quite small, providing longer separation times (and effective fractionation lengths) during which the fragment $F_i$ can become better resolved, i.e., further separated from the next closest size fragments.

Experiments conducted in support of the present invention show that the rate of migration of nucleic acid fragments through an uncharged fluid polymer matrix is subject to a number of variables related to fragment size, polymer concentration and type, and, where the electric field is produced by a pulsed voltage, to the pulse frequency of the field. The latter phenomenon will be described in Section D.

Figure 5:
FIG. 5 is an electropherogram of duplex DNA fragments fractionated in a buffer solution without polymer.

The migration rates of nucleic acid polymers in the absence of polymer in the capillary tube is shown in FIG. 5. The electrophoretic conditions are similar to those used in the electrophoretic separation shown in FIG. 4, except for the absence of polymer in the capillary medium. A comparison of the two figures shows first, that the fastest migrating species are the smallest molecular weight fragments (the peak centered around 4.047 minutes), and the slowest migrating species, the largest fragments (the peak centered around 4.381 minutes). Thus, the larger fragments appear to be migrating against the direction of electroosmotic flow faster than smaller fragments, possibly due to their greater total charge. Secondly, the only resolution provided by the system is between broad size classes, again reflecting an apparently gross difference in migration rate according to size.

Figure 6:
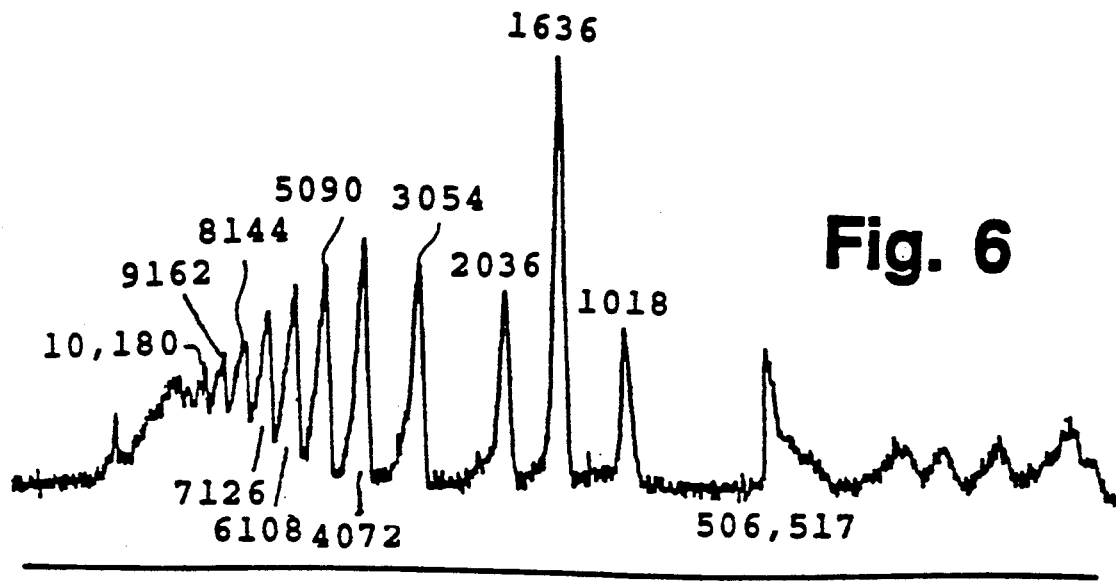
FIG. 6 is an electropherogram of duplex DNA fragments fractionated in accordance with the present invention, in 0.1 weight percent HPMC solution.

The effect of polymer concentration of the relative rates of migration of nucleic acid fragments is seen from FIG. 6, which is an electropherogram of nucleic acid restriction fragments fractionated in a 0.1 weight percent HPMC polymer. The fragments and fractionation conditions used are identical to those employed in the FIG. 4 method, except that the polymer concentration was about 2.5 fold lower. A comparison of the two figures shows that higher molecular weight fragments are better resolved at the lower polymer concentration, indicating that fragment migration rates for larger fragments cover a larger range with decreasing polymer concentration.

Figure 7:
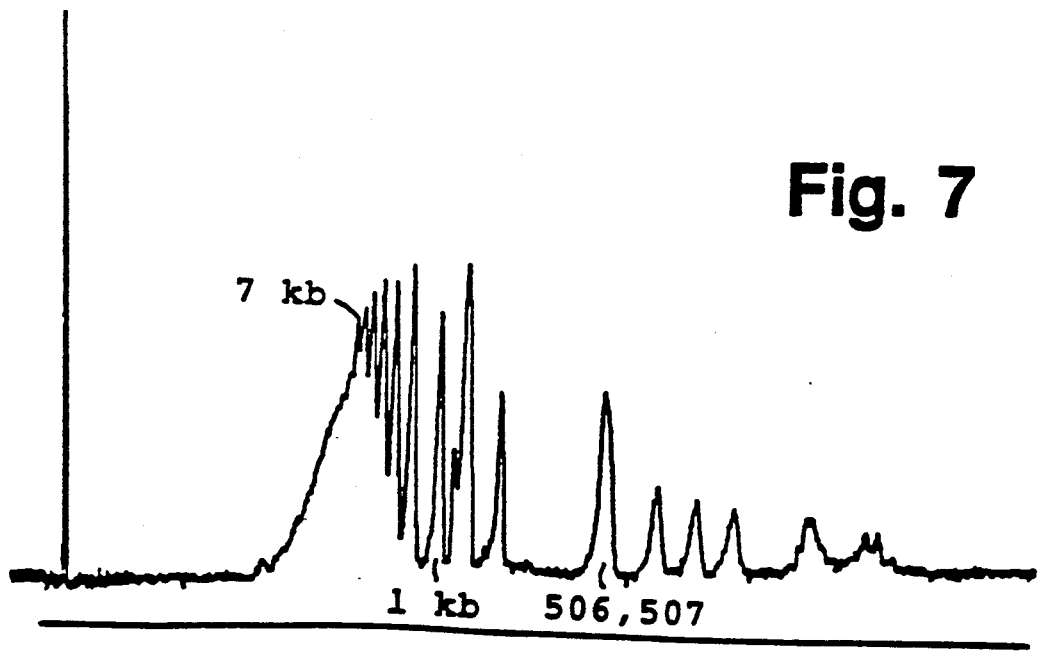
FIG. 7 is an electropherogram of duplex DNA fragments fractionated in accordance with the present invention, in a solution containing 0.25 weight percent hydroxyethylcellulose (HEC) polymer solution.

FIG. 7 shows an electropherogram of duplex fragments fractionated by CMCE in a 0.25 weight percent hydroxyethylcellulose (HEC) polymer solution. The polymer gave fractionation characteristics similar to those of 0.1 weight percent HPMC—sharper resolution of the fragments in the 1,000–7,000 kilobase ladder fragments, but less clarity of fractionation in the lowest molecular weight fragments with respect to CMCE fractionation in 0.25 weight percent HPMC. Little difference in the fragment fractionation pattern was observed when the concentration of HEC was reduced to 0.1 weight percent.

Figure 8:
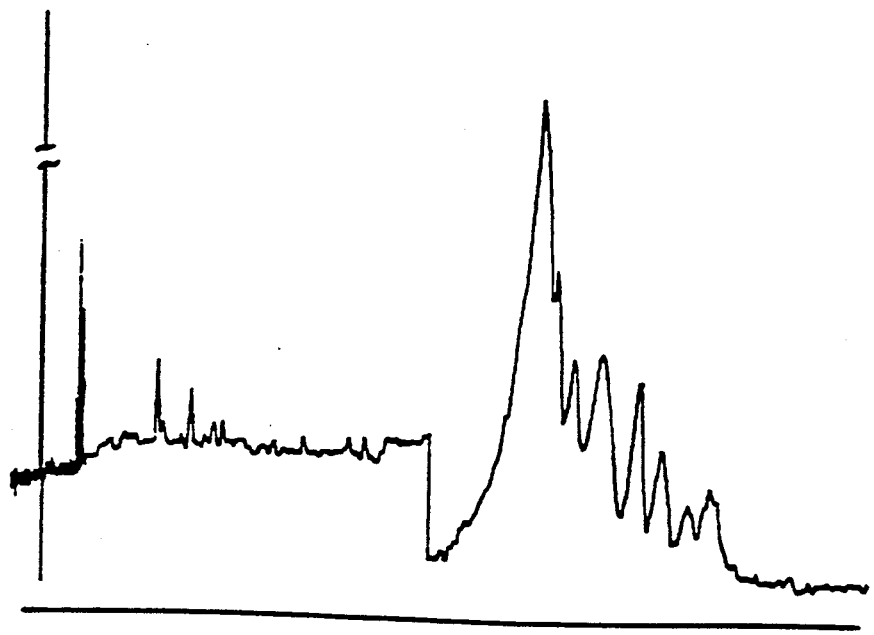
FIG. 8 is an electropherogram of duplex DNA fragments fractionated in accordance with the present invention, in a 1% dextran polymer solution.

FIG. 8 shows an electropherogram of duplex fragments fractionated by CMCE in a 1 weight percent dextran (MW=150,000). Although the polymer produces adequate resolution of fragments in the size range below about 1 kb, fragments above this range were not resolved. Lower concentrations of dextran and/or larger molecular weight dextran polymers may be necessary for improved resolution in the size range above 1 kilobase. Thus it is seen that resolution of selected size fragments can be enhanced according to the polymer used, e.g., HEC vs. HPMC, or the concentration of polymer e.g., 0.1 vs. 0.25 weight percent HPMC. Viewed another way, the migration rates of fragments through a polymer in the CMCE method may be a size-dependent function of both polymer type and polymer concentration.

According to another aspect of the invention, it has been discovered that the resolution among smaller size fragments can be selectively enhanced by complexing the fragments, preferably in double-strand form, with an intercalating agent. Exemplary intercalating agents include ethidium bromide and acridine orange. These agents share a flat, resonant molecular structure which allows the compounds to intercalate between adjacent bases of nucleic acids (Cantor). The agent is preferably included in the polymer solution drawn through the tube, to maintain the intercalating agent in quilibrium between free and DNA-bound forms.

Figure 9:
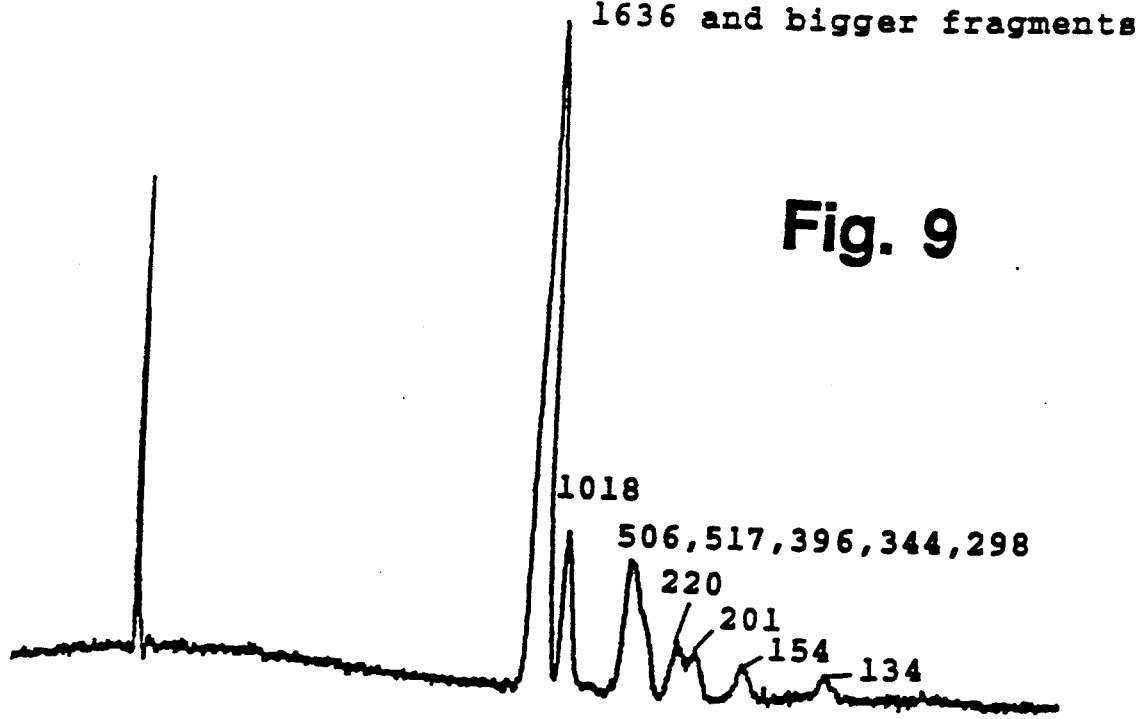
FIG. 9 is an electropherogram of duplex DNA fragments fractionated in accordance with the present invention, in 0.25 weight percent HPMC solution, in the presence of ethidium bromide.

FIG. 9 shows an electropherogram of the above duplex ladder fragments fractionated by CMCE in 0.25 weight percent HPMC in the presence of 10 μmole ethidium bromide. As seen from a comparison of this figure with FIG. 4, the intercalating agent enhances the resolution of fragments less than about 500 basepairs in size. This effect may be due to a size-dependent change in the conformation of the fragments when complexed with intercalating agent. A similar enhancement of small-fragment resolution was observed for acridine orange, another nonionic intercalating agent.

In addition, the relative rates of electroosmotic flow and fragment migration rates may be selectively adjusted by:

a. Changes in the electric field strength. In theory, the electric field E is directly proportional to the magnitude of both the bulk flow rate e and the migration rates of small charged particles through a non-polymer solution, for electric field strengths below 200 v/cm. However, in view of the fact that the order of fragment elution in the presence of polymer (FIG. 4) is opposite from that in the absence of polymer (FIG. 5), the migration of DNA through a polymer solution is evidently more complex than this model. In view of this, size-selective changes in net rates of migration may be achieved by adjusting the electric field strength, particularly in the range above 200 v/cm.

b. Changes in the charge density of the tube walls. The zeta potentials of the electric double layers of the column of polymer solution in the tube and that of the fragments in the polymer solution can be independently varied, e.g., by treating the surface of the tube to mask charge groups, or by adjusting the pH of the polymer solution to selectively protonate the tube wall charges or nucleic acid fragment charges.

c. Changes in solution viscosity. Although theory would predict that viscosity changes would effect electroosmotic flow and particle migration rate to the same extent, this prediction would likely not apply to large anionic solutes, such as nucleic acid fragments. Solution viscosity could be adjusted by changing the concentration of polymer (which has been shown to selectively alter fragment migration rates), by addition of polymers or other solute species which do not interact with nucleic acid fragments, and/or by changing the solution temperature.

Summarizing the above, the present invention provides a variety of parameters which may be selectively varied to enhance nucleic acid fractionation of selected sizes, either by selectively changing the rate of electroosmotic flow in the direction of the cathodic reservoir, or by differentially changing the upstream migration rates of the fragments being fractionated. As discussed above, the rate of electroosmotic flow, relative to counter migration of nucleic acid fragments, can be varied by changing the charge density of negatively charged groups on the inner capillary wall. The fragment migration rate in an anodic direction can be selectively reduced, for large fragments, by decreasing polymer concentration and/or according to the type of polymer. For shorter fragments, the rates of counter migration can be selectively increased by complexing the fragments with a nonionic intercalating agent. Such variations in flow and migrations rates are subject to the constraint that the electroosmotic flow be faster than the upstream fragment migration rate of the smallest fragments which is to fractionated.

D. Pulsed Field Separation

The electrophoretic methods described above were carried out under a constant-voltage field. In accordance with another aspect of the invention, the fractionation of nucleic acid fragments can be enhanced by carrying out the electrophoretic separation under a pulsed-voltage field, at a frequency effective to selectively enhance separation within a given fragment size range.

In theory, the migration rate behavior of nucleic acid fragments in a pulsed field may be governed by two size-related effects. The first effect is a resonance effect involving the fragment's rotational modes and the frequency of the electric field. Table I below shows rotational and stretching resonance frequencies which have been calculated for 100, 1,000, and 10,000 basepair duplex DNA fragments. The rotational resonance frequencies in Hz were calculated on the basis of a prolate ellipsoid model of the duplex molecule (Cantor).

TABLE I

| Model | Fragment Size (base pairs) | | |
|---|---|---|---|
| | 100 | 1000 | 10,000 |
| Prolate Elipsoid (rotational motion) | $9.9 \times 10^4$ | $1.6 \times 10^2$ | $2.2 \times 10^{-1}$ |
| Viscoelastic | $3.8 \times 10^5$ | $8.1 \times 10^3$ | $1.7 \times 10^2$ |

TABLE I-continued

| Model | Fragment Size (base pairs) | | |
|---|---|---|---|
| | 100 | 1000 | 10,000 |
| (stretching motion) | | | |

A strong rotational resonance effect predicts that the migration rates of fragments in resonance with the electric field will be preferentially slowed with respect to the migration rate in a time-invariant field. This is because a molecule in rotational resonance with the electric field would be expected to be, on average, least favorably oriented for migration in the direction of the field when the electric field is greatest. Larger molecules, because of their slower rotational times, would be expected to be less perturbed from their field-oriented positions at each voltage-pulse cycle; smaller molecules, with their faster response times, would more quickly reorient in the direction of the field. Thus, if rotational resonance effects are dominant, it should be possible to slow the migration of resonance species during electrophoresis relative to the electroosmotic flow rate and the rate of migration of non-resonance species.

Figure 10:
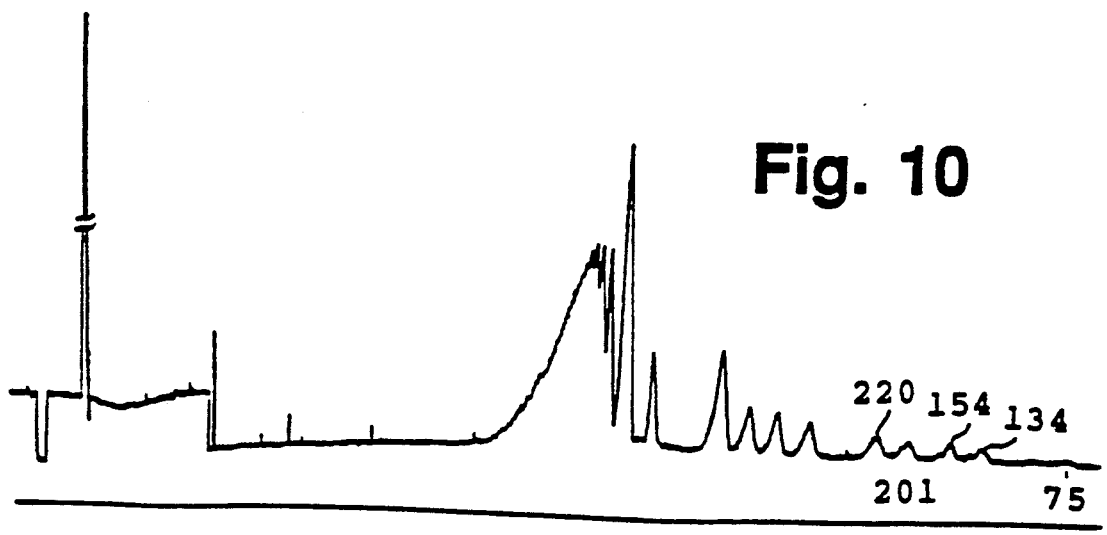
FIG. 10 shows a pulsed square wave and the corresponding migration rates of relatively large (dashed-dot line) and relatively small (dotted line) nucleic acid fragments during each voltage pulse.
Figure 11A:
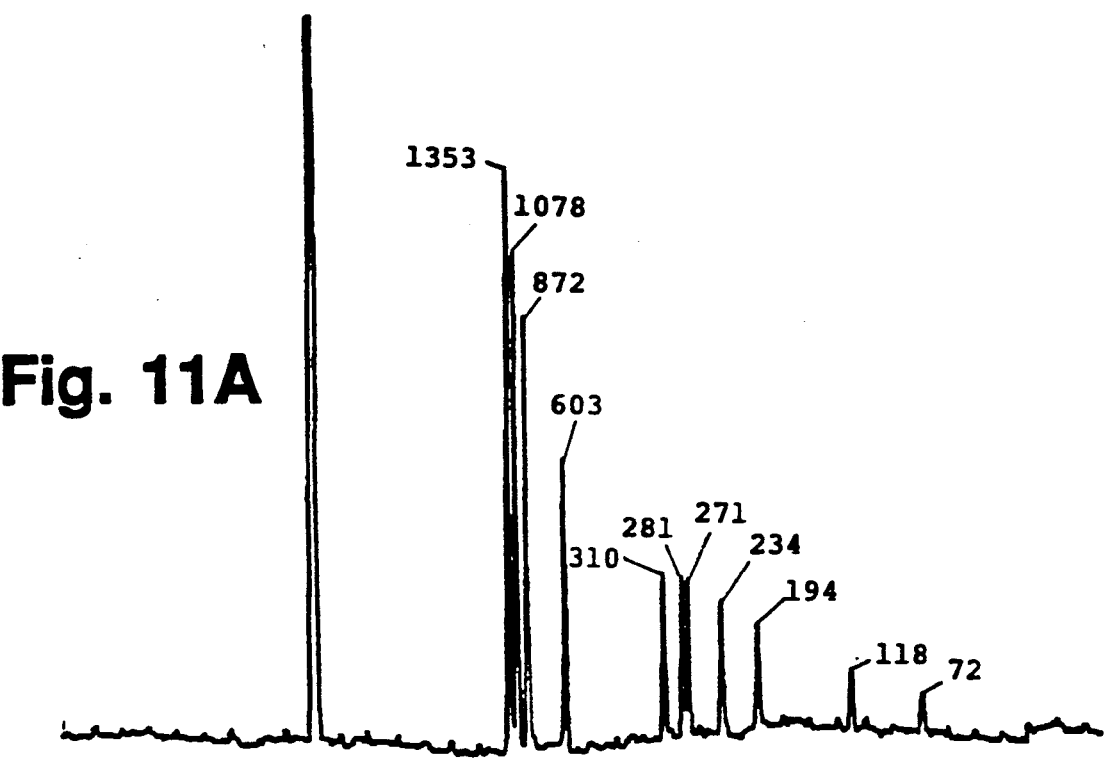
FIG. 11 shows the expected (dotted line) and observed (solid line) relationship between fragment size and migration rate with respect to migration rate in a constant-voltage field.
Figure 11B:
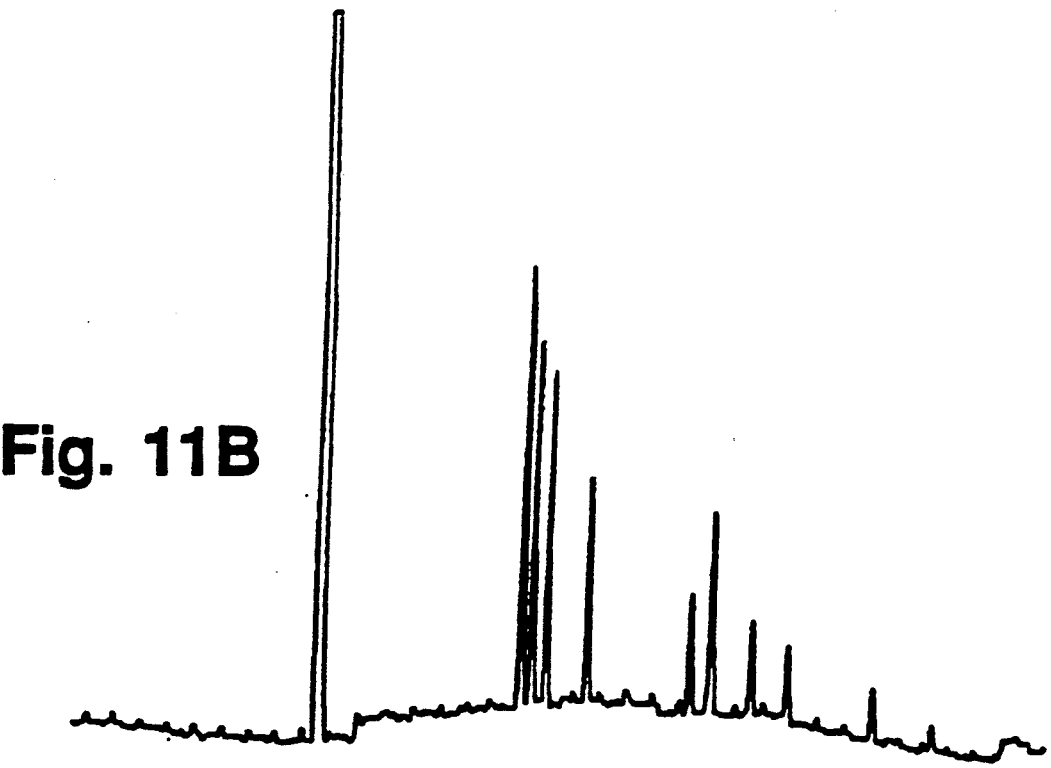
Figure 11C:
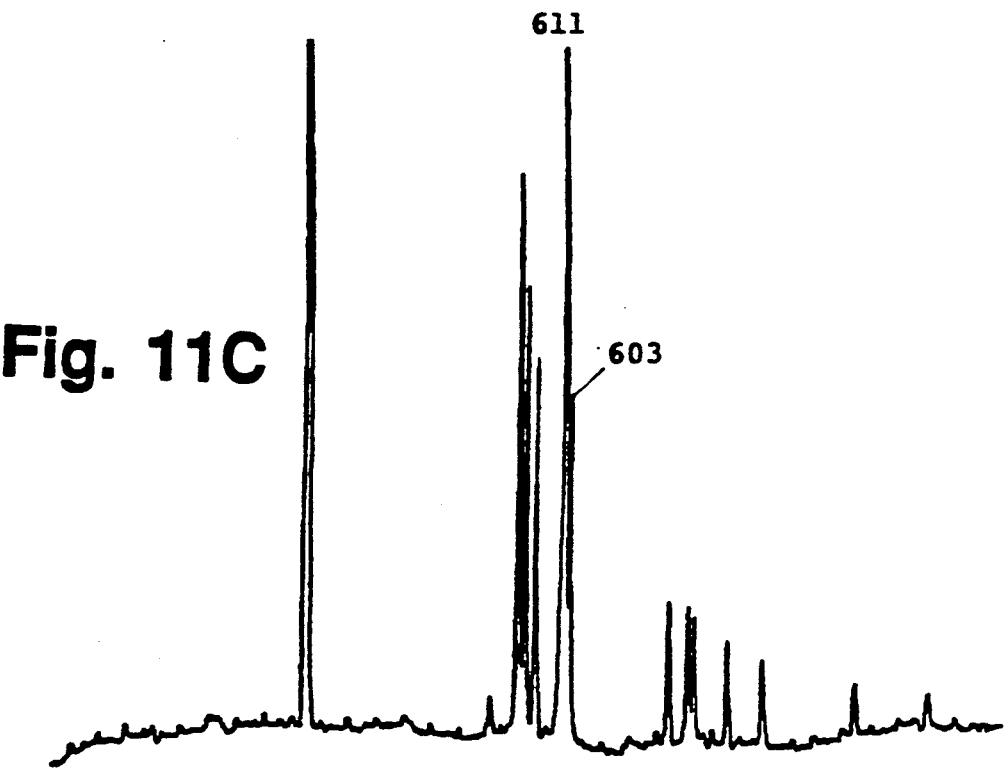
Figure 11D:
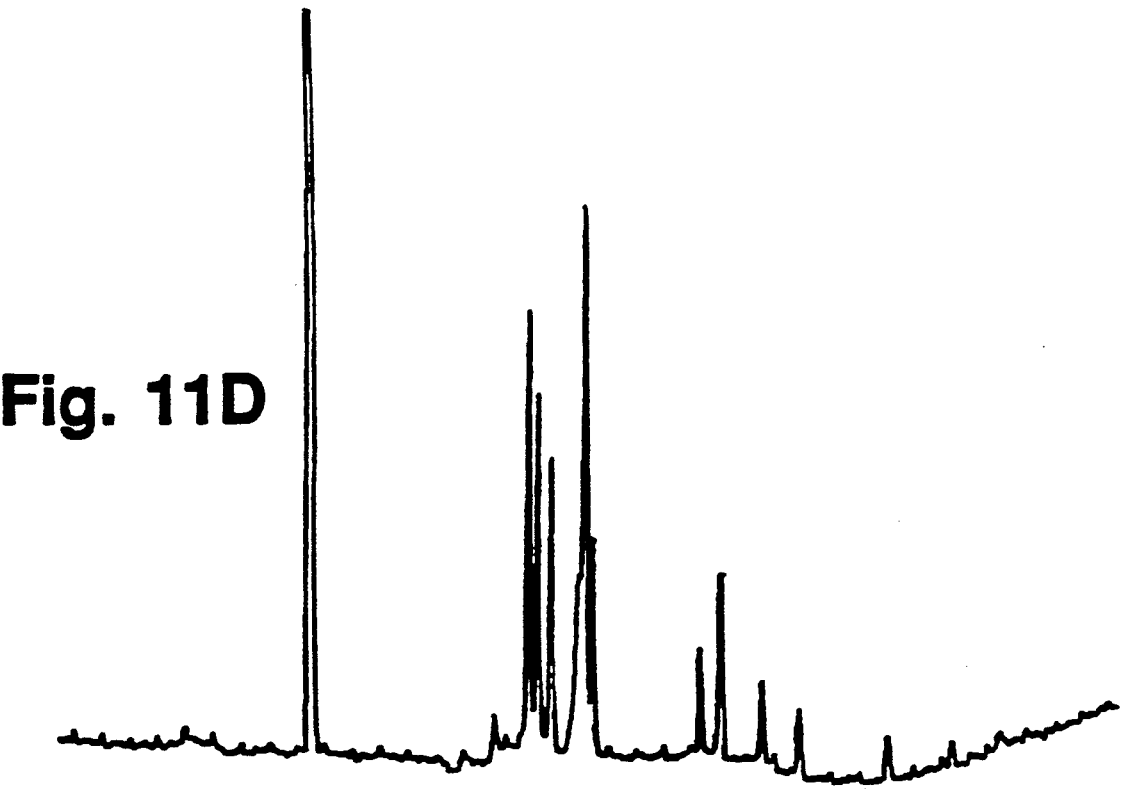

The second size-dependent effect which may might be expected in a pulsed field is an inertial effect due to the acceleration and deceleration of fragments in a fluid with each voltage pulse. This effect is illustrated in FIG. 10, which shows hypothetical velocity curves for relatively small (dotted lines) and relatively large (dash-dot lines) nucleic acid fragments, in relation to an applied square-wave voltage having a pulse width and a maximum voltage $v_{max}$. The maximum velocity which the fragments should reach is the terminal or steady-state velocity of the fragments in a constant voltage field of potential $v_{max}$, i.e., 100% of the constant field migration rate.

As seen from the figure, smaller fragments are expected to reach terminal velocity more rapidly than large ones after application of the voltage pulse, but to decelerate to zero voltage substantially at the same rate when the voltage pulse ends. Since the total distance traveled by each fragment during a voltage pulse is just the integral of the velocity curve, the migration rates of larger fragments are expected to be preferentially decreased in a pulse-voltage field. It can also be appreciated that the higher the pulse frequency and shorter pulse duration, the smaller the fragment size which can be preferentially retarded in its migration rate, since the effect of any lag in the velocity curve becomes accentuated at short pulses.

The dashed-line plot in FIG. 11 shows the expected effect relationship between migration rate, expressed as a percent of migration rate in a constant-voltage field and fragment molecular weight at a given pulse frequency. The plot has been normalized to correct constant voltage levels to rms voltage in a pulsed field. The dashed-line plot shows an increasing migration rate, with decreasing particle size, as predicted by the inertial model just discussed. At some small fragment size, where the velocity curves of the fragments tend toward a common upper limit, the migration rate approaches 100% migration in a constant-voltage field. The curve in FIG. 11 would therefore be expected to plateau at this point, as indicated by the dashed line.

Figure 12:
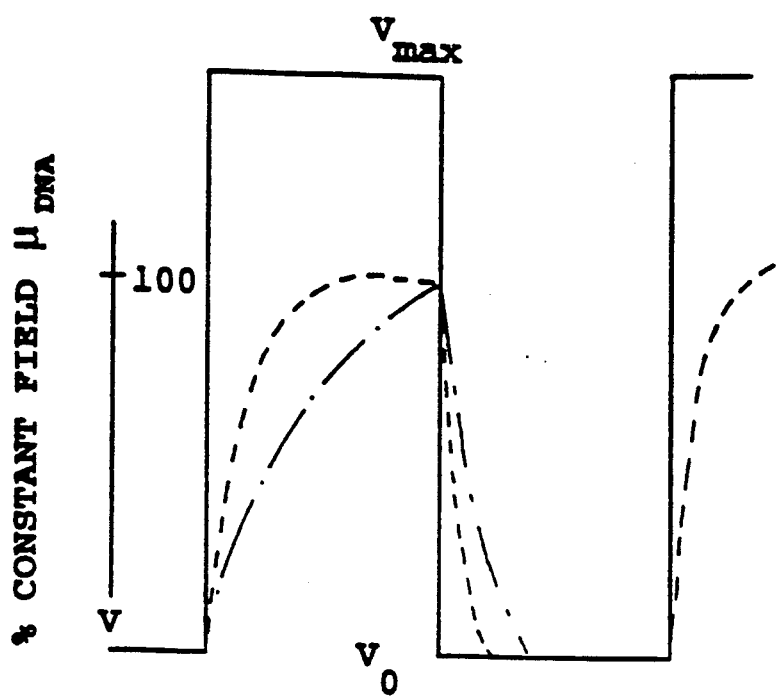
FIG. 12 is an electropherogram of duplex DNA fragments fractionated in accordance with the present invention, in 0.25 weight percent HPMC solution, at a pulsed field frequency of about 650 Hz.

FIG. 12 is an electropherogram of a mixture of duplex fragments fractionated in a pulsed field at 650 Hz. The sample material and fractionation conditions are similar to those used in the fractionation shown in FIG. 4, except for the nature of the applied electric field. The migration rates of the same size fragments were measured from the peak times in the two figures and compared, with the results shown in Table 2 below. Column A in the table gives the size, in basepairs, of the fragments which are compared, and column B, the difference in migration time to the detection zone, corrected for relative run times of the leading edge of the two runs, between v(constant), the rate in a constant-voltage field, and v(pulse), the rate in a pulsed field. The differences in velocity between corresponding fragments are expressed in cm/min $\times 10^{-4}$. A positive value in column B means the fragment has a lesser migration rate in a constant-voltage field than in a pulsed field. For fragments above 1 kilobase size, the v(pulse) approaches the v(constant) with decreasing size, as predicted by the FIG. 11 plot.

With smaller fragment sizes, however, the difference between v(constant) and v(pulse) does not plateau at a zero value, as would be expected from the inertial model, but continues to assume progressively more negative values with smaller fragments. The greater migration rate in a pulsed field would indicate that above the 100% crossover point, attractive interactions between the smaller fragments and the polymer are actually reduced, facilitating movement of the fragments through the polymer matrix. In any case, this feature provides greater resolution of smaller fragments above the "crossover" point than can be achieved under similar conditions in a constant voltage field.

TABLE II

| A<br>Frag. Size<br>(bp) | B<br>v (const.)-<br>v (pulse) |
|---|---|
| 2036 | 4.0E-04 |
| b | 4.1E-04 |
| a | 1.5E-04 |
| 1018 | 0.71E-04 |
| 396 | −3.8E-04 |
| 344 | −3.9E-04 |
| 298 | −4.5E-04 |
| 220 | −5.1E-04 |
| 201 | −5.2E-04 |
| 154 | −5.6E-04 |
| 134 | −5.5E-04 |
| 75 | −6.9E-04 |

It will be appreciated from the foregoing that the resolution among smaller size fragments can be selectively enhanced by carrying out the electrophoretic separation under a pulsed-voltage field, at a frequency which selectively retards the migration rate of larger fragments, and increases the migration rate of smaller fragments.

In some mixtures of nucleic acid fragments, particularly where it is desired to fractionate species in different size ranges, the variables discussed above—including solution pH, and polymer type and concentration, and field frequency — may be selectively varied during the electrophoretic run to enhance fragment resolution. For example, an electropheretic separation may be carried out under a constant field or low frequency initially, to resolve larger size fragment, then switched to a higher frequency to improve resolution of smaller size fragments. As another example, the pH or polymer concentration of the polymer solution can be continuously varied during an electrophoretic run, using a standard two-chamber mixing device to produce a continuous solution gradient which is drawn into the capillary tube.

E. Applications

The fractionation method of the invention finds utility in any of a variety of applications mentioned above requiring size fractionation of single-strand or duplex nucleic acids. These applications include electrophoretic separations for restriction analysis, including analysis of restriction fragment length polymorphisms for genetic screening, confirming vector construction, identifying specific nucleic acid fragments on the basis of size and/or hybridization to nucleic acid probes, and fractionating single-strand fragments for chemical or enzymatic sequencing.

The following two applications illustrate how the method may be used for restriction fragment analysis, and as part of an automated sequencing protocol. In the restriction analysis example, it is desired to identify, from a mixture of genomic fragments, a restriction fragment which contains a target sequence of interest. After digesting the genomic mixture with a selected restriction enzyme or enzyme(s), the fragment mixture is combined under hybridization conditions with reporter-labelled probe capable of hybridizing with the target sequence. The probe preferably includes the complementary target sequence and a covalently bound fluorescent probe which can be readily detected by a fluorescence probe detector. The probe may be hybridized with the fragments, for example, by standard denaturation/renaturation conditions involving single-strand species, or bound to the fragments in duplex form by RecA catalyzed triplex formation.

After binding the probe to the fragments, the sample is fractionated according to present CMCE method. The detector is preferably operated in a dual-wavelength mode, in which UV absorption and fluorescence emission detection are carried out concurrently.

Alternatively, the fragments of interest can be hybridized to a biotinylated probe, selectively isolated by binding to an avidin solid support, then released from the support prior to CMCE fractionation.

Figure 13:
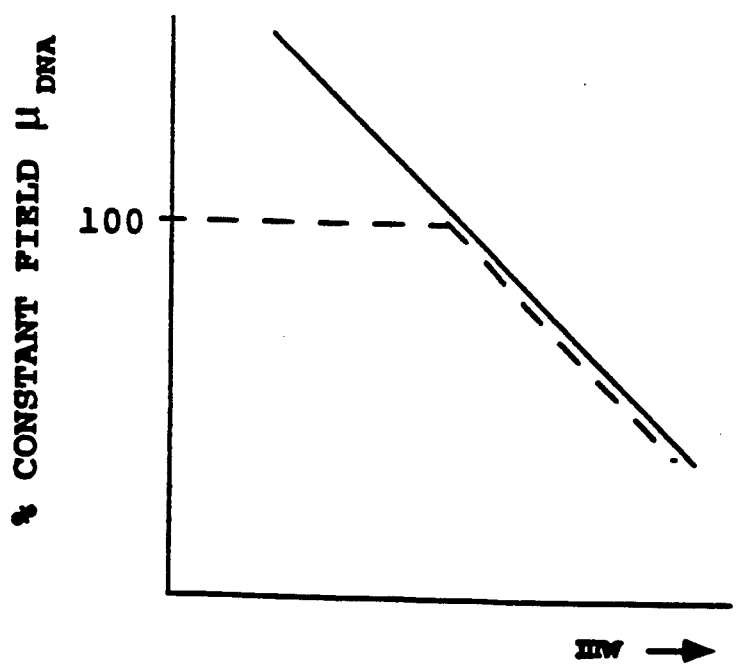
FIG. 13 is an electropherogram of polydeoxyadenylic acid (polyA) oligonucleotides fractionated in accordance with the invention in 1% weight percent HPMC solution.
Figure 14:
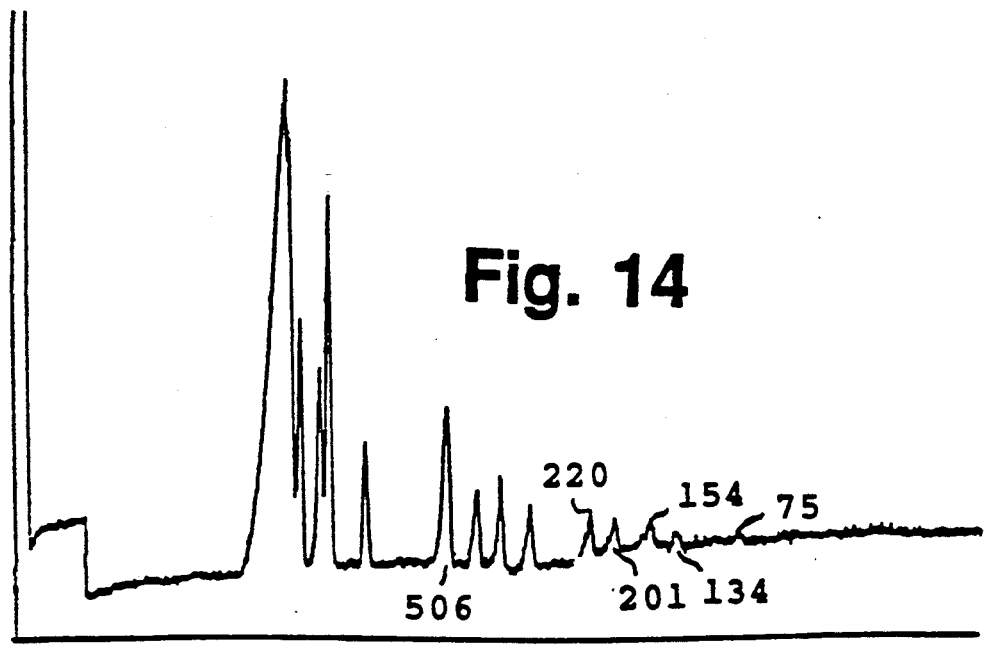
FIGS. 14A–14D illustrate model electropherograms obtained in a dideoxy chain termination sequencing method carried out in accordance with the invention.
Figure 16:
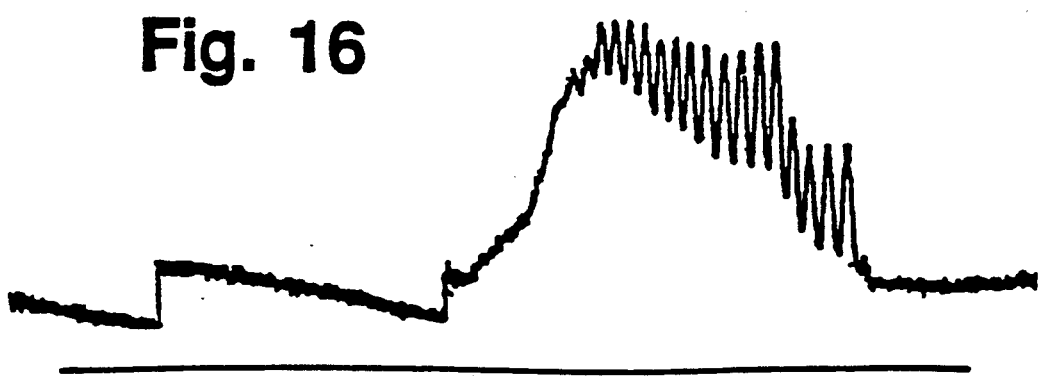
Figure 15:
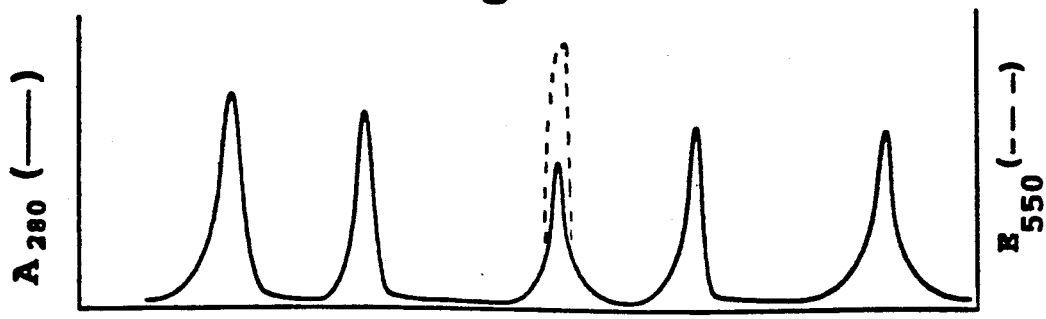
Figure 17A:
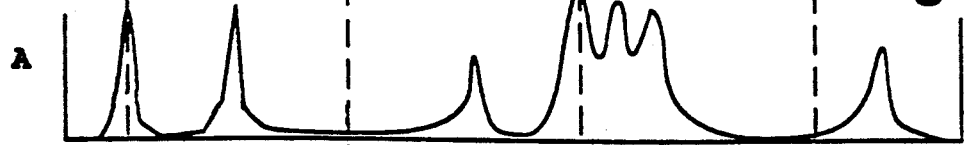
Figure 17B:
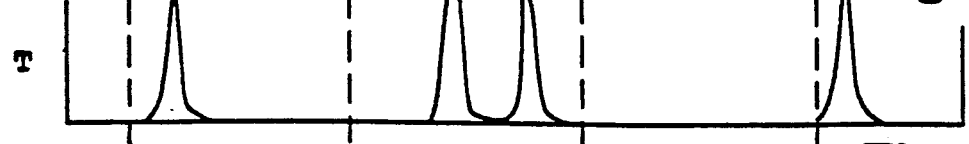
Figure 17C:
Figure 17D:

For DNA sequence analysis, it is necessary to resolve single-strand oligomers which differ from one another by one nucleotide base. The ability of the present method to achieve resolution of this type is illustrated in FIG. 13, which shows an electropherogram for a mixture of polyA oligonucletides containing all basepair lengths between 40 and 60 basepairs. The figure shows that all 20 of the different-size oligomers are well resolved. Similar resolution of oligomers in the 19-22 basepair range has been achieved, as detailed in Example 7.

The oligomers used for sequencing may be prepared by the dideoxy enzyme method (Sanger) or chemical cleavage method (Maxam-Gilbert). The oligonucleotide fragments from the four separate reaction mixtures are fractionated, preferably in parallel, and the fragment peaks from each of the four tubes is recorded. FIGS. 14A-14D show oligonucleotide electropherograms from the A, T, G, C -terminated fragments as would be observed for the nucleotide sequence shown at the top in the figure. Automated or semi-automated analysis of the peak positions and construction of the sequence can be performed using standard programed systems.

Alternatively, the oligonucleotide fractionation may be carried out in a single tube using, for example, the fluorescence labeling method described by Smith.

The following examples illustrate various separation methods and applications in accordance with the invention, but are in no way intended to limit the scope thereof.

EXAMPLE 1

Constant Field CMCE in 0.25% HPMC Polymer

Counter-migration capillary electrophoresis (CMCE) was
out using an ABI Model 270 capillary electrophoresis system. The system includes a built-in high-voltage DC power supply capable of voltage settings up to 30 KV. The capillary tube used in the system is a fused silica capillary tube 72 cm long with a 50 $\mu$m i.d. and 350 $\mu$m o.d.obtained from Polymicro Technologies (Phoenix, AZ).

The grounded cathodic reservoir is filled with Trisborate-EDTA buffer containing 10 mM Tris-borate, pH 8.3, 5 mM NaCl, 0.1 mM EDTA, and 7 M urea (TBE buffer). The anodic reservoir contained a polymer solution containing 0.25 weight percent hydroxypropylmethylcellulose (HPMC) in TBE buffer. The polymer, which is characterized by a viscosity of about 4,000 centipoise in a 2% by weight solution at room temperature, was obtained by Dow Chemical (Midland, MI).

The tube was washed with several column volumes of 1M NaOH, then 100 mM NaOH, and finally flushed with several volumes of the polymer solution, by drawing the wash and flush solutions through the tube by a vacuum applied to the cathodic end of the tube. A DNA restriction fragment mixture obtained from BRL (Bethesda, MD) contained a combination of 1 kb ladder partial restriction fragments (multiples of about 1 kB) and smaller HinfI digest fragments in the size range between about 50–1,000 basepair. The fragment mixture was diluted with water to a final DNA concentration of about 250 $\mu$g/ml. About 2 nanoliters of the DNA solution was drawn into the anodic end of the tube by vacuum applied to the cathodic tube end. The tube was then reimmersed in the polymer solution.

The electrophoretic system was run at a voltage setting of about 20 kV (about 400 V/cm) throughout the run. UV detection was with a Kratos 783 UV detector designed for capillary tube detection. The detector output signal was integrated and plotted on an HP Model 3396A integrator/plotter.

The electropherogram obtained is shown in FIG. 4. The numbers above the major peaks are electrophoresis times, in minutes. Total run time was about 11 minutes. The sizes of the fragments in the fractionated mixture, expressed in number of basepairs, are in boldface print. As seen, the method effectively separated fragments in the range 75 to about 3,000 basepairs, and gave distinct peaks for fragments in the range 3,000 to 6,000 basepairs. The fragment molecular weights were confirmed by known standards.

EXAMPLE 2

Constant Field CMCE without Polymer

The electrophoretic method described in Example 1 was followed, except that the TBE buffer solution used for fragment separation did not contain polymer, and the voltage setting was about 800 V/cm. The electropherogram of the fractionated DNA material is shown in FIG. 5. In contrast to the electro-pherograms in FIGS. 4, the smallest fragments (centered at about 4.047 minutes migration time) traveled fastest toward the cathode, indicating that the smallest fragments were actually traveling most slowly toward in the upstream direction toward the cathode. There is no significant resolution among the fragments except for broad size ranges, and elution peaks of all of the fragments were closely spaced.

EXAMPLE 3

Constant Field CMCE in 0.1% HMPC

The electrophoretic method described in Example 1 was employed, except that the polymer solution used for fragment separation contained 0.1% weight percent HPMC polymer. The electropherogram of the fractionated DNA material is shown in FIG. 6. It is apparent from this figure that the lower polymer concentration allowed good peak resolution up to about 10 kb fragment sizes, with some loss of resolution of fragments below the size range of about 500 basepairs.

EXAMPLE 4

Constant Field CMCE in 0.25% HEC Polymer

The electrophoretic method described in Example 1 was employed, except that the TBE polymer solution used for fragment separation contained 0.25 weight percent hydroxyethylcellulose (HEC) polymer. The HEC polymer was obtained from Dow Chemical (Midland, MI), and had a viscosity of about 300 centipoise in a 2% solution at room temperature. The electropherogram of the fractionated DNA material is shown in FIG. 7. Interestingly, the electropherogram shows resolution of ladder peaks in the 2,000–8,000 Kbase size region, with less sharp resolution of the smallest peaks, when compared with the 0.25% HMPC separation shown in FIG. 4. Similar results were obtained by CMCE fractionation in 0.1% HEC, although the resolution of both high and low molecular weight species was better at the higher polymer concentration. Polymer solutions of methylcellulose (MC), including 0.25 weight percent MC, gave very good resolution of the smaller-size fragments (less than 500 bp).

EXAMPLE 5

Constant Field CMCE in 1% Dextran Polymer

The electrophoretic method described in Example 1 was employed, except that the TBE polymer solution used for fragment separation contained 1% dextran polymer. The polymer was obtained from Sigma (St Louis, MO) and had an average molecular weight of about 150,000. The electropherogram of the fractionated DNA material is shown in FIG. 8. The fragments were less well resolved in this polymer than in either the HMPC or HEC polymers.

EXAMPLE 6

Constant Field CMCE in 0.25% HMPC plus Ethidium Bromide

The DNA ladder fragment mixture from Example 1 was mixed with ethidium bromide, to a final 10 $\mu$M ethidium bromide concentration. The CMCE polymer solution was a TBE buffer with 0.25% HPMC polymer and 10 $\mu$M ethidium bromide. CMCE fractionation was carried out as in Example 1, with the results shown in FIG. 9. A comparison of this figure with FIG. 4 shows substantially greater resolution of fragments in the size range up to about 1-2 kilobases, and some loss of resolution at higher molecular weights, with respect to CMCE fractionation in the absence of intercalating agent.

A similar electrophoretic separation was carried out on the same partial digest fragments prepared in a polymer solution containing 2.6 μM acridine orange. The results were similar to those obtained with ethidium bromide, showing enhanced resolution of lower molecular weight species.

EXAMPLE 7

Constant Field CMCE of Single-Stranded DNA

A mixture of polyA oligonucleotides containing between 40–60 nucleotides was obtained from Pharmacia (Uppsala, Sweden). The oligonucleotide mixture was dissolved in water to 350 μg/ml. About 2 nanoliters of sample solution was drawn into the anodic end of the tube by vacuum applied to the cathodic tube end, and the material was fractionated in a 0.25% HPMC polymer, at a constant-voltage of about 140 v/cm. Total run time was about 30 minutes. The electropherogram obtained is shown in FIG. 13. It is seen that the CMCE fractionation effectively resolved each of the 20 oligomers in the mixture. A mixture of smaller oligonucleotides, in the 19-22 basepair size range were similarly resolved by this method.

EXAMPLE 8

Pulsed Field Electrophoretic Separation

The mixture of partial digest DNA ladder fragments and HinfI fragments from Example 1 was loaded at the cathodic end of a capillary tube as in Example 1. A pulsed voltage was generated using an HP 3314A function generator (for generating a square wave), a Krohn-Hite Model 7500 amplifier, and a Jefferson Electric high-voltage transformer. The applied voltage had a peak voltage of about 25 kV, and an RMS voltage of about 12.5 kV, giving an applied RMS voltage of about 170 V/cm, and a pulse frequency of 650 Hz. The power supply was operated in a pulsed voltage mode for about 45 minutes, at which point the leading edge of the fractionation mixture was just upstream of the detection zone. The power supply was then switched to a constant voltage mode, at about 12.5V/cm, until the end of the electrophoretic separation.

The electropherogram obtained by the method is shown in FIG. 12. The numbers above the major peaks are electrophoresis times, in minutes, after switching the DC mode. The size of the fragments in the fractionated mixture, expressed in basepairs, are given in boldface print. The peak positions obtained were compared with those in FIG. 4, which gives peak fragment migration times for the same peaks under constant-field electrophoresis conditions. The changes in peak migration rates, as a function of size, are discussed above with respect to Table 2. Briefly, fragments larger than about 2,000 basepairs migrated more slowly in a pulsed field, whereas smaller fragments migrated more rapidly with respect to the normalized rates of migration in a constant-voltage field.

While the invention has been described with respect to specific embodiments, methods, and applications, it will be recognized by those skilled in the art that of modifications of the method and application of the method to other uses involving nucleic acid fractionation may be made without departing from the invention.

It is claimed:

1. A method of fractionating a mixture of different molecular weight nucleic acid fragments, comprising
   loading a liquid sample containing the nucleic acid fragments into one end of a microcapillary tube filled with a fluid electrolyte solution, where the inner wall surface of the tube contains negatively charged groups, one end of the tube is placed in fluid communication with an anodic reservoir containing a polymer solution of an uncharged polymer having a molecular weight of at least about 50,000 daltons, and the other tube end is placed in communication with an cathodic reservoir, and
   applying a voltage between the anodic and cathodic reservoirs which is effective to draw said polymer solution into and through the tube by electroosmotic flow, at a fluid flow rate in the tube which is greater, in the direction of the cathodic reservoir, than the molecular-weight dependent rates of migration of such nucleic acid fragments, in the direction of the anodic reservoir, such larger molecular weight nucleic acid fragments move more rapidly toward the cathodic reservoir.

2. The method of claim 1, for use in enhancing the fractionation of selected molecular weight nucleic acid fragments, which further includes adjusting the rate of electroosmotic flow of polymer solution in the direction of the cathodic reservoir or the rate of fragment migration through the polymer solution in the direction of the anodic reservoir, to reduce the difference between the flow rate and the migration rates of the selected molecular weight fragments, thereby to increase the effective tube length over which electrophoretic migration of the fragments can occur.

3. The method of claim 2, wherein said adjusting includes decreasing the concentration of the polymer solution, to increase preferentially the differential fragment migration rates of relatively large polymers through the polymer.

4. The method of claim 2, wherein the fragments are doublestranded, and said adjusting includes adding an intercalating agent to the fragments, to increase preferentially the migration rates of smaller molecular weight fragments through the polymer solution.

5. The method of claim 4, wherein the intercalating agent is selected from the group consisting of ethidium bromide and acridine orange.

6. The method of claim 2, wherein the voltage applied between said reservoirs is a pulsed voltage, and said adjusting includes selecting a pulsed voltage frequency at which the migration rates of the selected molecular weight fragments are increased with respect to the rates in a constant electrical field of the same field strength.

7. The method of claim 6, wherein the nucleic acid fragments are in the size range 100 to 2,000 basepairs, and the frequency of the pulsed voltage applied is between about 100-500 Hz.

8. The method of claim 6, wherein said applying includes applying a pulsed voltage at one selected frequency which enhances separation of the selected size fragments from larger fragments, and applying a pulsed voltage and a second, different selected frequency which enhances separation of the selected size fragments from smaller fragments.

9. The method of claim 1, wherein the polymer in the polymer solution is a polysaccharide whose molecular weight is at least about 100,000 daltons.

10. The method of claim 9, wherein said polymer is selected from the group consisting of dextran and water-soluble cellulose derivatives.

11. The method of claim 1, for use in fractionating doublestranded nucleic acid fragments in the size range of about 20 to 5,000 base pairs, which further includes adding an intercalating agent to the fragments prior to said loading.

12. The method of claim 1, which further includes detecting the presence of fragment bands at a given position adjacent the cathodic end of the tube, by measuring an optical property of the fragments in the tube.

13. The method of claim 12, for use in performing restriction digest analysis of a DNA sample, which further comprises digesting the sample with one or more selected restriction endonucleases.

14. The method of claim 12, for use in identifying, in a mixture of DNA fragments, a fragment having a selected target basepair sequence, which further includes hybridizing the fragment with a single-strand nucleic acid probe containing a sequence which is complementary to the target sequence, and detecting the fragment having the target sequence on the basis of its binding to the probe.

15. The method of claim 12, for use in determining the sequence of a single-strand nucleic acid fragment, which further includes treating the fragment to generate four sets of randomtermination fragments which terminate at one of the nucleic acid bases, and by said detecting, determining the migration rates of each of the fragments in each of the four fragment sets.

16. A method of fractionating a mixture of different molecular weight nucleic acid fragments, comprising
loading a liquid sample containing the nucleic acid fragments into one end of a microcapillary tube filled with a fluid electrolyte solution, where the inner wall surface of the tube contains negatively charged groups, one end of the tube is placed in fluid communication with an anodic reservoir containing a polymer solution of an uncharged polymer having a molecular weight of at least about 50,000 daltons, and the other tube end is placed in communication with an cathodic reservoir, and
applying a pulsed voltage between the anodic and cathodic reservoirs which is effective to draw said polymer solution into and through the tube by electroosmotic flow, at a fluid flow rate in the tube which is greater, in the direction of the cathodic reservoir, than the molecular-weight dependent rates of migration of such nucleic acid fragments, in the direction of the anodic reservoir, such larger molecular weight nucleic acid fragments move more rapidly toward the cathodic reservoir, and
adjusting the frequency of the pulsed voltage to increase the migration rates of the selected molecular weight fragments with respect to the rates in a constant electrical field of the same field strength.

17. The method of claim 16, wherein said adjusting includes applying a pulsed voltage at one selected frequency which enhances separation of the selected size fragments from larger fragments, and applying a pulsed voltage and a second, different selected frequency which enhances separation of the selected size fragments from smaller fragments.

18. A method of fractionating a mixture of different molecular weight nucleic acid fragments, comprising
loading a liquid sample containing the nucleic acid fragments into one end of a microcapillary tube filled with a fluid electrolyte solution, where the inner wall surface of the tube contains negatively charged groups, one end of the tube is placed in fluid communication with an anodic reservoir containing a polymer solution containing an intercalating agent and an uncharged polymer having a molecular weight of at least about 50,000 daltons, and the other tube end is placed in communication with an cathodic reservoir, and
applying a voltage between the anodic and cathodic reservoirs which is effective to draw said polymer solution into and through the tube by electroosmotic flow, at a fluid flow rate in the tube which is greater, in the direction of the cathodic reservoir, than the molecular-weight dependent rates of migration of such nucleic acid fragments, in the direction of the anodic reservoir, such larger molecular weight nucleic acid fragments move more rapidly toward the cathodic reservoir.

19. The method of claim 18, wherein the intercalating agent is selected from the group consisting of ethidium bromide and acridine orange.

* * * * *